United States Patent [19]

McCombie

[11] 4,212,860

[45] Jul. 15, 1980

[54] 4-O-(2,3,5-TRIDEOXY-5-AMINO-α-D-PENTOFURANOSYL)-6-O-AMINOGLYCOSYL-1,3-DIAMINOCYCLITOIS, METHODS FOR THEIR PREPARATION, PHARMACEUTICAL FORMULATIONS THEREOF AND THEIR USE AS ANTIBACTERIAL AGENTS

[75] Inventor: Stuart McCombie, West Orange, N.J.

[73] Assignee: Schering Corporation, Kenilworth, N.J.

[21] Appl. No.: 959,032

[22] Filed: Nov. 8, 1978

Related U.S. Application Data

[63] Continuation-in-part of Ser. No. 922,605, Jul. 7, 1978, abandoned.

[51] Int. Cl.² ...................... A61K 31/71; C07H 15/22
[52] U.S. Cl. ................................ 424/180; 260/347.7; 536/10; 536/17 R
[58] Field of Search ..................... 424/180; 536/10, 17

[56] References Cited

U.S. PATENT DOCUMENTS

| | | | |
|---|---|---|---|
| 3,049,552 | 8/1962 | Garber | 260/346.11 |
| 3,268,560 | 8/1966 | Heying | 260/346.11 |
| 4,065,616 | 12/1977 | Umezawa et al. | 536/10 |
| 4,101,556 | 7/1978 | Kavadias et al. | 536/17 |

OTHER PUBLICATIONS

Kugelman et al. Reprint from "Jour. of the Chem. Soc." Perkins Transactions I, 1976, pp. 1097–1113.
Mallams et al. Reprint from "Jour. of the Chem. Soc." Perkins Transactions I, 1976, pp. 1135–1146.

*Primary Examiner*—Johnnie R. Brown
*Attorney, Agent, or Firm*—Mary S. King

[57] ABSTRACT

4-O-(2,3,5-Trideoxy-5-amino-α-D-pentofuranosyl)-6-O-aminoglycosyl-1,3-diaminocyclitols and 1-N-substituted derivatives thereof are described together with methods for their preparation and their use as antibacterial agents.

Preferred are 1-N-(ω-amino-α-hydroxyalkanoyl)-[4-O-(2,3,5-trideoxy-5-amino-α-D-pentofuranosyl)-6-O-garosaminyl-2-deoxystreptamines], particularly the 1-N-(S-β-amino-α-hydroxypropionyl) derivatives, which are broad spectrum antibacterial agents.

14 Claims, No Drawings

4-O-(2,3,5-TRIDEOXY-5-AMINO-α-D-PENTOFURANOSYL)-6-O-AMINOGLYCOSYL-1,3-DIAMINOCYCLITOLS, METHODS FOR THEIR PREPARATION, PHARMACEUTICAL FORMULATIONS THEREOF AND THEIR USE AS ANTIBACTERIAL AGENTS

CROSS REFERENCE TO RELATED APPLICATION

This application is a continuation-in-part of my copending application Ser. No. 922,605 filed July 7, 1978, now abandoned.

FIELD OF INVENTION

This invention relates to novel compositions-of-matter, to methods for their manufacture, to methods for their use as antibacterial agents and to pharmaceutical formulations useful therefor.

More specifically, this invention relates to 4-O-(2,3,5-trideoxy-5-amino-α-D-pentofuranosyl)-6-O-aminoglycosyl-1,3-diaminocyclitols having antibacterial activity, to methods for their manufacture, to pharmaceutical compositions comprising said 4-O-(2,3,5-trideoxy-5-amino-α-D-pentofuranosyl)-6-O-aminoglycosyl-1,3-diaminocyclitols and to methods for their use in treating bacterial infections.

In particular, this invention relates to 4-O-(2,3,5-trideoxy-5-amino-α-D-pentofuranosyl)-6-O-garosaminyl-2-deoxystreptamine and the 5-epi-, 5-deoxy-, 5-epi-amino-5-deoxy-, 5-epi-azido-5-deoxy-, 5-fluoro-5-deoxy, and 5-epi-fluoro-5-deoxy-derivatives thereof as well as the 1-N-substituted derivatives of the foregoing, including 1-N-alkyl- and 1-N-acyl- derivatives which may be substituted by hydroxyl and/or amino functions.

This invention also relates to processes for preparing the foregoing compounds, to pharmaceutical compositions comprising said 4-O-(2,3,5-trideoxy-5-amino-α-D-pentofuranosyl)-6-O-garosaminyl-2-deoxystreptamine derivatives and to the method of using said pharmaceutical compositions to elicit an antibacterial response in a warm blooded animal having a susceptible bacterial infection.

PRIOR ART

Naturally occurring aminoglycoside antibiotics having a pentofuranose sugar unit are known (e.g., butirosin A, butirosin B and Streptomycin), but none of these have a structure similar to the 4,6-di-O-(aminoglycosyl)-2-deoxystreptamine structure characteristic of the gentamicin group of antibiotics.

Also known (A. K. Mallams et al, J. Chem. Soc. (Perkin Transactions I) 1097–1113, 1135–1146 (1976)) are synthetically prepared garamine derivatives having a pentofuranose or 2-deoxypentofuranose ring linked to the 4-oxygen which have no known useful biological activity.

By my invention, I have discovered a method to prepare garamine derivatives having the heretofore unknown 2,3,5-trideoxy-5-amino-α-D-pentofuranose ring linked to the 4-oxygen, said derivatives exhibiting antibacterial activity.

GENERAL DESCRIPTION OF THE INVENTION COMPOSITION-OF-MATTER ASPECT

Included among the antibacterially active compositions-of-matter of this invention are 4-O-(2,3,5-trideoxy-5-amino-α-D-pentofuranosyl)-6-O-aminoglycosyl-1,3-diaminocyclitols wherein said 6-O-aminoglycosyl is a member selected from the group consisting of garosaminyl, 3-desmethylgarosaminyl, 4-desmethylgarosaminyl, 4-desmethyl-4-epigarosaminyl, 3,4-bisdesmethylgarosaminyl, and 3,4-bisdesmethyl-4-epigarosaminyl, and wherein said 1,3-diaminocyclitol is 2-deoxystreptamine or a 5-epi-, 5-deoxy-, 5-fluoro-5-deoxy-, 5-epi-fluoro-5-deoxy, 5-epi-azido-5-deoxy- or a 5-epi-amino-5-deoxy- derivative thereof;

and the 1-N-substituted derivatives thereof wherein said substituent is —CH₂X or

wherein X is a member selected from the group consisting of hydrogen, alkyl, alkenyl, cycloalkyl, cycloalkylalkyl, hydroxyalkyl, aminoalkyl, N-alkylaminoalkyl, aminohydroxyalkyl, N-alkylaminohydroxyalkyl, phenyl, benzyl, or tolyl, said substituent having up to 8 carbon atoms, and when substituted by both amino and hydroxyl groups, bearing said groups on different carbon atoms;

and the pharmaceutically acceptable acid addition salts thereof.

Contemplated for the moiety "X" in the 1-N-substituted derivatives of my novel compounds are straight and branched chain alkyl groups such as methyl, ethyl, n-propyl, n-butyl, β-methylpropyl, n-pentyl, β-methylbutyl, γ-methylbutyl, β,β-dimethylpropyl, n-hexyl, δ-methylpentyl, β-ethylbutyl, γ-ethylbutyl, n-heptyl, β-ethylpentyl, γ-ethylpentyl, δ-ethylpentyl, γ-propylbutyl; cycloalkyl groups such as cyclopropyl, cyclobutyl, cyclohexyl, and cycloheptyl; cycloalkylalkyl groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl; aralkyl groups such as benzyl, o-tolyl, m-tolyl, p-tolyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyheptyl; amino substituted straight and branched chain alkyl groups such as ε-aminopentyl, β-aminopropyl, γ-aminopropyl, δ-aminobutyl, β-amino-γ-methylbutyl and ω-aminoheptyl and mono-N-alkylated derivatives thereof such as the N-methyl, N-ethyl, and N-propyl derivatives, e.g., ε-methylaminopentyl, β-methylaminopropyl, β-ethylaminopropyl, δ-methylaminobutyl, β-methylamino-γ-methylbutyl, and ω-methylaminobutyl; amino and hydroxy disubstituted straight and branched chain alkyl groups such as β-hydroxy-ε-aminopentyl, γ-hydroxy-γ-methyl-δ-aminobutyl, α-hydroxy-δ-aminobutyl, α-hydroxy-γ-aminopropyl, α-hydroxy-β-aminoethyl, and β-hydroxy-β-methyl-γ-aminopropyl; and mono-N-alkylated derivatives thereof such as β-hydroxy-ε-methylaminopentyl, γ-hydroxy-γ-methyl-δ-methylaminobutyl, β-hydroxy-δ-methylaminobutyl, α-hydroxy-γ-ethylaminopropyl, α-hydroxy-β-methylaminoethyl, and β-hydroxy-β-methyl-γ-methylaminopropyl.

Particularly useful compounds of my invention are those wherein the 6-O-aminoglycosyl is 6-O-garosaminyl and the 1,3-diaminocyclitol is 2-deoxystreptamine as well as the 5-epi-, 5-deoxy-, 5-fluoro-5-deoxy-, 5-epi-fluoro-5-deoxy-, 5-epi-azido-5-deoxy-, and 5-epi-amino-5-deoxy- derivatives thereof. Of these, the most valuable as antibacterial agents are those having a

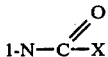

substituent wherein X is an α-hydroxy-ω-aminoalkyl having 2 to 4 carbon atoms, i.e., wherein the

substituent is α-hydroxy-γ-aminopropionyl, α-hydroxy-δ-aminobutyryl, or α-hydroxy-ω-aminovaleryl. Thus, preferred compounds of this invention include 4-O-(2,3,5-trideoxy-5-amino-α-D-pentofuranosyl)-6-O-garosaminyl-2-deoxystreptamine and the 1N-(ω-amino-α-hydroxyalkanoyl) derivatives thereof wherein said alkanoyl has 3 to 5 carbon atoms, a particularly valuable compound being 1-N-(S-δ-amino-α-hydroxypropionyl)-[4-O-(2,3,5-trideoxy-5-amino-α-D-pentofuranosyl)-6-O-garosaminyl-2-deoxystreptamine].

It is to be noted that the 1-N-(ω-amino-α-hydroxyalkanoyl) substituents in the foregoing compounds of my invention may be in the R,S,- form or in the R- form or in the S- form. In accordance with this invention, each of the foregoing names includes all three forms so that the name 1-N-(δ-amino-α-hydroxypropionyl)-[4-O-(2,3,5-trideoxy-5-amino-α-D-pentofuranosyl)-6-O-garosaminyl-2-deoxystreptamine] includes the 1-N-(S-δ-amino-α-hydroxypropionyl)-, the 1-N-(R-δ-amino-α-hydroxypropionyl)-, and the 1-N-(R,S-δ-amino-α-hydroxypropionyl) derivatives of 4-O-(2,3,5-trideoxy-5-amino-α-D-pentofuranosyl)-6-O-garosaminyl-2-deoxystreptamine.

Also included within the composition-of-matter aspect of this invention are pharmaceutically acceptable acid addition salts of 4-O-(2,3,5-trideoxy-5-amino-α-D-pentofuranosyl)-6-O-garosaminyl-2-deoxystreptamine and derivatives thereof, which salts are made according to known procedures such as by neutralizing the free base with the appropriate acid, usually to about pH 5. Suitable acids for this purpose include hydrochloric, sulfuric, phosphoric, hydrobromic and the like. The physical embodiments of the acid addition salts are characterized by being white solids which are soluble in water and insoluble in most polar and nonpolar organic solvents.

The 4-O-(2,3,5-trideoxy-5-amino-α-D-pentofuranosyl)-6-O-aminoglycosyl-1,3-diaminocyclitols of this invention (particularly those wherein the 6-O-aminoglycosyl is 6-O-garosaminyl and the 1,3-diaminocyclitol is 2-deoxystreptamine) and their nontoxic, pharmaceutically acceptable acid addition salts in general, exhibit broad spectrum antibacterial activity, being active against gram-positive bacteria (e.g., *Staphylococcus aureus* and *Bacillus subtilis*) and gram-negative bacteria (e.g., *Escherichia coli* and *Pseudomonas aeruginosa*) as determined by standard dilution tests. Advantageously, they are active against bacteria which inactivate the kanamycins and gentamicin B by 3'-O-phosphorylation and 4'-O-adenylylation and, in general, are less acutely toxic than gentamicin C complex.

In addition to the foregoing, the preferred compounds of this invention, i.e., 1-N-(ω-amino-α-hydroxyalkanoyl)-[4-O-(2,3,5-trideoxy-5-amino-α-D-pentofuranosyl)-6-O-aminoglycosyl-2-deoxystreptamine] and their pharmaceutically acceptable acid addition salts are also active against organisms which inactivate aminoglycosides of the gentamicin and kanamycin groups by acetylation of the 3-amino group or by adenylylation of the 2''-hydroxyl group while also possessing a low order of toxicity. For example, a preferred compound of this invention, i.e., 1-N-(S-β-amino-α-hydroxypropionyl)-[4-O-(2,3,5-trideoxy-5-amino-α-D-pentofuranosyl)-6-O-aminoglycosyl-2-deoxystreptamine] exhibits a high order and a broad spectrum of antibacterial activity similar to that of 1-N-(γ-amino-α-hydroxypropionyl)gentamicin B including activity against 2''-adenylylating and 3-N-acetylating strains, while being much less acutely toxic than the gentamicin C complex, i.e., being only about as toxic as gentamicin B$_1$.

That the 4-O-(2,3,5-trideoxy-5-amino-α-D-pentofuranosyl)-6-O-garosaminyl-2-deoxystreptamine derivatives of this invention (which may also be called 4-O-(2,3,5-trideoxy-5-amino-α-D-pentofuranosyl)garamine or O-(2,3,5-trideoxy-5-amino-α-D-pentofuranosyl) (1→4) garamine derivatives) possess antibacterial activity is surprising when one considers that prior art 4-O-(pentofuranosyl)- and 4-O-(2-deoxyfuranosyl)-garamine derivatives described by A. K. Mallams et al (J. Chem. Soc., Perkin Transactions I, 1097–1113, 1135–1146 (1976)), do not exhibit antibacterial activity. For example, it has been found that none of 4-O-α-(2-deoxy-2-aminoglucofuranosyl)garamine, the 4-O-β-isomer thereof (compounds 45 and 47, respectively, on page 1102 of A. K. Mallams et al), 4-O-β-D-ribosylgaramine, 4-O-β-(2-deoxy-D-ribosyl)garamine or 4-O-α-(2-deoxy-D-ribosyl)garamine (compounds 2 and 4 on page 1135 and compound 16 on page 1137, respectively, of A. K. Mallams et al) exhibit any detectable antibacterial activity at 25 mcg/ml or less when tested in the standard dilution test.

Another composition-of-matter aspect of my invention resides in the concept of novel intermediates which are 1,3,3''-tri-N-protected-5,2'',4''-tri-O-protected derivatives of 4-O-(2,3,5-trideoxy-5-azido (or 5-amino or 5-N-protected amino)-α-D-pentofuranosyl)-6-O-aminoglycosyl-1,3-diaminocyclitols wherein said 6-O-aminoglycosyl and said 1,3-diaminocyclitol are as hereinabove defined and wherein all hydroxyl functions and amino functions are protected by groups susceptible to reductive cleavage (such as by treatment with hydrogen in the presence of a catalyst or by treatment with an alkali metal in liquid ammonia) or to basic hydrolysis (such as with aqueous sodium hydroxide) which compounds are useful in preparing the antibacterially active 4-O-(2,3,5-trideoxy-5-amino-α-D-pentofuranosyl)-6-O-aminoglycosyl-1,3-diaminocyclitols of this invention.

The terms "amino protecting group" and "hydroxy protecting group" are well known in the art and refer to a large number of groups suitable for temporarily protecting an amino or hydroxyl function in a molecule from undergoing chemical reactions, yet are readily removed after a desired chemical reaction has taken place. The choice of the protecting group depends on whether a hydroxy or amino group is being protected, subsequent reaction conditions, and conditions for removal, which choice is within the ability of one skilled in the art. The amino and hydroxy protecting groups which are most useful in this invention are those stable to acid and which are removable by treatment with base.

Useful amino protecting groups for the intermediates of this invention include lower alkoxycarbonyls (preferably having up to 8 carbon atoms, e.g., methoxycarbonyl, ethoxycarbonyl, n-propyloxycarbonyl, isopropyloxycarbonyl, n-butyloxycarbonyl, tert.-butoxycarbonyl, octyloxycarbonyl and the like), substituted benzyloxycarbonyl (including o, m and p-methoxybenzyloxycarbonyl, and the like) and, preferably, benzyloxycarbonyl. Lower alkanoyls preferably having up to 8 carbon atoms (e.g., acetyl, propionyl, valeryl, caprylyl) are also useful amino protecting groups. The foregoing amino protecting groups are removable by treatment with base (e.g., with sodium hydroxide) or, in the case of benzyloxycarbonyl or substituted benzyloxycarbonyls, also removable by reductive cleavage methods known in the art. Benzyloxycarbonyl is a preferred amino protecting group because it is removed under the reducing conditions of the process of this invention whereby an N,O-protected-(2,3,5-trideoxy-5-azido-α-D-pentofuranosyl)-6-O-aminoglycosyl-1,3-diaminocyclitol intermediate is treated with hydrogen in the presence of a catalyst (i.e., palladium) or with an alkali metal (e.g., sodium or potassium) in liquid ammonia to produce (after alkaline hydrolysis) an N,O-unprotected-(2,3,5-trideoxy-5-amino-α-D-pentofuranosyl)-6-O-aminoglycosyl-1,3-diaminocyclitol antibacterially active compound of this invention.

Hydroxyl functions in the intermediates of this invention are conveniently protected by O-acyl radicals of hydrocarboncarboxylic acids preferably having up to 8 carbon atoms or by O-hydrocarbonylidene radicals of ketones and aldehydes preferably having up to 8 carbon atoms to form ketals and acetals, respectively, including cyclic ketals and acetals. The preferred O-protecting groups are benzoyloxy or lower alkanoyloxy, acetoxy being particularly useful.

Of the N,O-protected-4-O-(2,3,5-trideoxy-5-azido-α-D-pentofuranosyl) intermediates, a particularly valuable compound is 1,3,3″-tri-N-benzyloxycarbonyl-5,2″,4″-tri-O-acetyl-[4-O-(2,3,5-trideoxy-5-azido-α-D-pentofuranosyl)-6-O-aminoglycosyl-2-deoxystreptamine] which, upon reduction followed by alkaline hydrolysis, produces directly 4-O-(2,3,5-trideoxy-5-amino-α-D-pentofuranosyl)-6-O-garosaminyl-2-deoxystreptamine, a preferred compound of this invention.

The method of preparing the novel N,O-protected-(2,3,5-trideoxy-5-azido-α-D-pentofuranosyl)-6-O-aminoglycosyl-1,3-diaminocyclitols is described in detail in the Examples and in the Process Aspect of the Invention, the processes for introducing and removing said protecting groups being well known in the art.

Yet another composition-of-matter aspect of this invention resides in the concept of novel lactol derivatives which are S-5-(azidomethyl (or aminomethyl or N-protected aminomethyl))-2-lower alkoxy-tetrahydrofuran, said lower alkoxy preferably having up to four carbon atoms, said compounds having the following formula I:

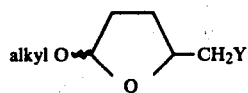

wherein Y is azido, amino or N-protected amino. The above novel compounds are useful in the preparation of the N,O-protected-4-O-(2,3,5-trideoxy-5-azido (or 5-N-protected amino)-α-D-pentofuranosyl)-6-O-aminoglycosyl-1,3-diaminocyclitol intermedaites discussed hereinabove and described in detail hereinbelow in the Examples and in the Process Aspect section.

Most useful compounds of formula I are the S-5-(azidomethyl)-2-alkoxytetrahydrofurans, a preferred compound being S-5-(azidomethyl)-2-ethoxytetrahydrofuran.

PROCESS ASPECT OF THE INVENTION

The process sought to be patented resides in the concept of a process for the preparation of a 4-O-(2,3,5-trideoxy-5-amino-α-D-pentofuranosyl)-6-O-(aminoglycosyl)-1,3-diaminocyclitol antibacterial compound of this invention as defined hereinabove and in the claims, which comprises the reaction of an N-protected-O-protected-6-O-aminoglycosyl-2-deoxystreptamine having an unprotected-4-hydroxyl group or a 5-epi-, 5-deoxy-, 5-fluoro-5-deoxy-, 5-epi-fluoro-5-deoxy-, 5-epi-azido-5-deoxy-, or a 5-epi-N-protected-amino-5-deoxy-derivative thereof, wherein said 6-O-aminoglycosyl is a member selected from the group consisting of garosaminyl, 3-desmethylgarosaminyl, 4-desmethylgarosaminyl, 4-desmethyl-4-epi-garosaminyl, 3,4-desmethyl-garosaminyl, and 3,4-desmethyl-4-epigarosaminyl, with a lactol derivative selected from the group consisting of an S-5-(azidomethyl)-2-lower alkoxytetrahydrofuran and an S-5-(N-protected aminomethyl)-2-lower alkoxytetrahydrofuran, said lower alkoxy having up to four carbon atoms, in an inert organic solvent and in the presence of acid, said N- and O-protecting groups being stable to acid and removable by treatment with base;

and, when said lactol derivative is S-5-(azidomethyl)-2-lower alkoxytetrahydrofuran, followed by reaction of the thereby formed N-protected-O-protected-4-O-(2,3,5-trideoxy-5-azidomethyl-α-D-pentofuranosyl)-6-O-aminoglycosyl-1,3-diaminocyclitol with a reducing agent;

and thence removal of the N-protecting and O-protecting groups from the resulting N-protected-O-protected-4-O-(2,3,5-trideoxy-5-aminomethyl (or 5-N-protected aminomethyl)-α-D-pentofuranosyl)-6-O-aminoglycosyl-1,3-diaminoayclitol.

In brief, this process comprises the preparation of the novel N-protected-O-protected trisaccharide-5′-azido (or 5′-N-protected amino-)- intermediates of this invention by the acid catalyzed condensation of an S-5-(azidomethyl (or N-protected aminomethyl))-2-lower alkoxytetrahydrofuran (novel lactol derivatives of formula I) with an N-protected-O-protected-disaccharide having a free 4-hydroxyl function (e.g., 1,3,3′-tri-N-benzyloxycarbonyl-5,2′,4′-tri-O-acetylgaramine) with removal of alcohol followed by reduction of the 5′-azido function when the lactol employed is an S-5-(azidomethyl-2-lower alkoxytetrahydrofuran) and thence removal of the O- and N-protecting groups.

The N-protecting and O-protecting groups contemplated for use in my process are acid stable protecting groups and removable by base as disclosed in detail in the composition-of-matter section hereinabove, a preferred N-protecting group being benzyloxycarbonyl and a preferred O-protecting groups being acetyl.

The suitably N,O-protected disaccharide starting compounds (i.e., the N-protected-O-protected-6-O- aminoglycosyl-1,3-diaminocyclitols having a free 4-hydroxyl function) are either known compounds or are prepared via procedures well known in the art.

Preferred disaccharide starting compounds include N,O-protected garamine (also called N,O-protected-6-O-garosaminyl-2-deoxystreptamine) which is known and conveniently prepared via cleavage of N-protected sisomicin either by acid hydrolysis or oxidative routes such as described in U.S. Pat. No. 4,063,015, said garamine derivatives having the following formula II:

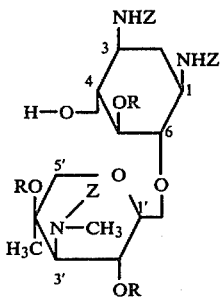

wherein Z is an amino protecting group and R is a hydroxyl protecting group.

A preferred intermediate of formula II is one wherein Z is benzyloxycarbonyl and R is acetyl, i.e., 1,3,3'-tri-N-benzyloxycarbonyl-5,2',4'-tri-O-acetylgaramine.

Similarly, the 5-epi-, 5-deoxy, 5-fluoro-5-deoxy, 5-epifluoro-5-deoxy-, 5-epi-azido-5-deoxy-, and 5-epi-N-protected amino-5-deoxy-garamine are preferred starting compounds which are prepared utilizing procedures similar to those described in U.S. Pat. No. 4,063,015 via cleavage of the corresponding N,O-protected sisomicin derivative, i.e., N,O-protected derivatives of 5-episisomicin, 5-deoxysisomicin, 5-fluoro-5-deoxysisomicin, 5-epifluoro-5-deoxysisomicin, 5-epi-azido-5-deoxysisomicin, and 5-epiamino-5-deoxysisomicin. Most of the foregoing sisomicin precursors are known. 5-Epifluoro-5-deoxysisomicin is prepared by reaction of an N,O-protected-sisomicin having an unprotected 5-hydroxyl group with diethylaminosulfur trifluoride in a manner described in South African Pat. No. 78/0385 (Jan. 20, 1978) claiming as priority U.S. Ser. No. 792,825 filed May 2, 1977, now abandoned, in favor of continuation-in-part application Ser. No. 893,638, filed Apr. 4, 1978. Similarly, 5-fluoro-5-deoxysisomicin is prepared by reaction of an N,O-protected-5-epi-sisomicin having an unprotected 5-epihydroxyl group with diethylaminosulfur trifluoride.

The disaccharide starting compounds N,O-protected-4'-desmethylgaramine, N,O-protected-4'-desamethyl-4'-epigaramine, and N,O-protected-3'-desmethylgaramine and their 5-epi, 5-deoxy-, 5-fluoro-5-deoxy-, 5-epifluoro-5-deoxy, 5-epi-azido-5-deoxy-, and 5-epi-amino-5-deoxy analogs are prepared via hydrolytic cleavage of the corresponding N-protected Antibiotic 66-40D, N-protected Antibiotic 66-40B, N-protected-3''-desmethylsisomicin on their 5-epi-, 5-deoxy-, 5-fluoro-5-deoxy-, 5-epi-fluoro-5-deoxy-, 5-epi-azido-5-deoxy and 5-epi-amino-5-deoxy analog, in a manner described in Preparation 5 followed by O-protection of the hydroxyl functions except at C-4 via known techniques such as described in Preparation 8.

3'-Desmethylgaramine may also be prepared from garamine by reaction with iodine and sodium acetate in aqueous methanol utilizing known techniques. In similar manner, 3',4'-desmethylgaramine and 3',4'-desmethyl-4'-epigaramine are derived from 4'-desmethylgaramine and 4'-desmethyl-4'-epigaramine, respectively.

The preferred lactol derivatives of this process, i.e., the S-5-(azidomethyl)-2-lower alkoxytetrahydrofurans (compounds of formula I wherein Y is azido), are prepared from L-glutamic acid in a multi-step process described in Preparations 1 to 4, and are useful in preparing all the compounds of this invention with the exception of the 5-epi-azido-5-deoxy compounds. When utilizing a compound of formula I wherein Y is azido, the trisaccharide intermediate formed is an N-protected-O-protected-4-O-(2,3,5-trideoxy-5-azidomethyl-α-D-pentofuranosyl)-6-O-aminoglycosyl-1,3-diaminocyclitol which must be reduced to convert the 5-azidomethyl function in the pentofuranosyl ring to the desired 5-aminomethyl function. When N-benzyloxycarbonyl derivatives are used as N-protecting groups, they are advantageously cleaved simultaneously with the reduction of the 5-azidomethyl group. Also, it is obvious if a 5-epiazido-5-deoxy starting disaccharide (e.g., an N,O-protected-6-O-garosaminyl-5-epi-azido-2,5-dideoxystreptamine) is condensed with an S-5-(azidomethyl)-2-lower alkoxytetrahydrofuran that the 5-epi-azido function in the dideoxystreptamine ring of the resulting trisaccharide intermediate will reduce to the corresponding 5-epi-amino function concomitantly with the reduction of the 5-azidomethyl group to the 5-aminomethyl group in the pentofuranosyl ring. Thus, when a 5-epi-azido-5-deoxy-trisaccharide compound of this invention is being prepared by my process utilizing a 5-epi-azido-5-deoxy-disaccharide starting compound, the lactol derivative of choice is an S-5-(N-protected-aminomethyl)-2-lower alkoxytetrahydrofuran, preferred N-protecting groups being N-ethoxycarbonyl and N-phthalimido. When 5-N-protected aminomethyl lactol derivatives are used in my process, reduction of the trisaccharide intermediate is unnecessary and the 5-epi-azido-5-deoxy function in the N,O-protected trisaccharide intermediate remains unchanged; thus, upon removal of the N and O-protecting groups there is produced a 5-epi-azido-5-deoxy compound of this invention, e.g., 4-O-(2,3,5-trideoxy-5-amino-α-D-pentofuranosyl)-5-epi-azido-5-deoxygaramine.

The 5-N-protected aminomethyl lactols may be prepared utilizing known techniques from the corresponding 5-aminomethyl lactol which, in turn, is prepared by reduction of the corresponding 5-azidomethyl lactol. Thus, for example, S-5-(azidomethyl)-2-ethoxytetrahydrofuran, upon treatment with hydrogen in the presence of palladium catalyst, is converted to S-5-(aminomethyl)-2-ethoxytetrahydrofuran which, upon reaction with ethyl chloroformate and sodium carbonate according to known procedures produces S-5-(N-ethoxycarbonylaminomethyl)-2-ethoxytetrahydrofuran. Reaction of the foregoing with N-protected-O-protected-5-deoxy-5-epi-azido-garamine according to my process will produce N-protected-O-protected-4-O-(2,3,5-trideoxy-5-(N-ethoxycarbonylaminomethyl)-α-D-pentofuranosyl)-6-O-garosaminyl-2,5-dideoxy-5-epi-azidostreptamine which, upon treatment with base will produce the corresponding unprotected derivative of this invention, i.e., 4-O-(2,3,5-trideoxy-5-aminomethyl-α-D-pentofuranosyl)-6-O-garosaminyl-2,5-dideoxy-5-epi-azidostreptamine.

Alternatively, S-5-(N-phthalimidomethyl)-2-ethoxytetrahydrofuran, another useful lactol derivative for preparing 5-epi-azido-5-deoxy compounds of this invention, may be prepared directly from S-5-(p-toluenesulfonyloxymethyl)-2-ethoxytetrahydrofuran (described hereinbelow in Preparation 4B) by reaction with potassium phthalimide utilizing known techniques.

The condensation step in the process of this invention is carried out in the presence of catalytic quantites of an acid, preferably a fairly strong, non-carboxylic acid such as phosphoric, sulfuric, methanesulfonic, and preferably p-toluenesulfonic acid.

The condensation step of the process must be carried out at a temperature sufficiently high to remove the lower alkanol being displaced by the condensation between the 4-hydroxy of the disaccharide intermediate and the 2-alkoxy group of the lactol intermediate. Usually, temperatures slightly above the boiling point of the alcohol being removed, or higher, are employed; although if one employs a solvent which co-distills with the displaced alcohol, the reaction can be carried out at such co-distillation boiling point.

The process is carried out in an inert organic solvent in the absence of water. By "inert organic solvent" is meant any organic solvent in which the starting compounds and reagents are soluble and which will not interfere with the process under the specific reaction conditions so as to insure a minimum of competing side reactions. Anhydrous aprotic solvents are preferred such as dioxane, tetrahydrofuran, chloroform, nitromethane, 1,2-dichloroethane, toluene and, preferably, benzene.

The reduction step of my process whereby the N-protected-O-protected-4-O(2,3,5-trideoxy-5-azido-α-D-pentofuranosyl)-6-O-aminoglycosyl-1,3-diaminocyclitol is reduced to the corresponding 5-amino function, charide intermediate to a 5-aminomethyl function. The O-protecting groups are then removed by basic hydrolysis to produce a 4-O-(2,3,5-trideoxy-5-amino-α-D-pentofuranosyl)-garamine derivative of our invention.

In a preferred mode of carrying out my process, a mixture of an N-protected-O-protected garamine derivative (e.g., 1,3,3'-tri-N-benzyloxycarbonyl-5,2',4'-tri-O-acetylgaramine) is reacted with about from 1 to 1.3 molar equivalents of an S-5-(azidomethyl)-2-alkoxytetrahydrofuran (preferably S-5-(azidomethyl)-2-ethoxytetrahydrofuran) in an anhydrous, aprotic solvent (e.g., benzene) and in the presence of catalytic quantities of an acid (e.g., p-toluenesulfonic acid) at moderately elevated temperatures, usually at solvent distillation temperatures (usually about 80° C.) so as to remove the alkanol (e.g. ethanol) by-product. When the reaction is complete (usually in about two hours) as indicated by the absence of N,O-protected garamine in the reaction mixture as determined by thin layer chromatography, the resulting N-protected-O-protected-4-O-(2,3,5-trideoxy-5-azido-α-D-pentofuranosyl)-garamine derivative (e.g., 1,3,3''-tri-N-benzyloxycarbonyl-5,2'',4''-tri-O-acetyl-[4-O-(2,3,5-trideoxy-5-azido-α-D-pentofuranosyl)-6-O-garosaminyl-2-deoxystreptamine]) is isolated and purified utilizing known techniques.

In the condensation step of the process as illustrated hereinbelow, the lactol derivative, i.e., S-5-(azidomethyl)-2-ethoxytetrahydrofuran (II'), in the presence of acid easily forms an oxonium ion in intermediate (A) which, under the conditions of the reaction, loses ethanol forming an oxocarbonium ion (B) which adds on to the garamine intermediate (II) to form exclusively an α-glycoside of this invention (III).

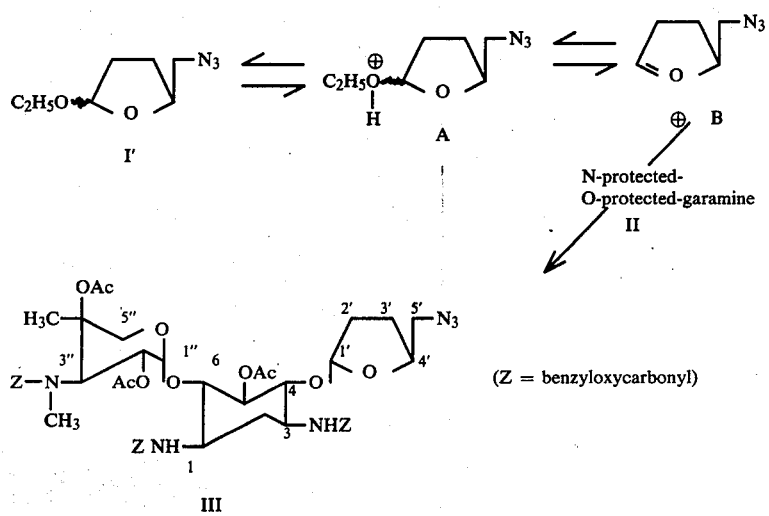

is usually carried out with hydrogen in the presence of a catalyst, although reduction by means of an alkali metal in ammonia may be employed. When reducing with hydrogen in the presence of a catalyst, the catalysts most frequently employed are platinum, palladium and, preferably, palladium-on-charcoal. The hydrogenation is usually carried out at room temperatures in aqueous dioxane, although other solvents such as ethanol or aqueous tetrahydrofuran may be employed.

When the garamine disaccharide starting compounds are N-protected with groups susceptible to reductive cleavage, e.g., by benzyloxycarbonyl, the N-protecting groups are removed in the reduction step concomitantly with reduction of the 5-azidomethyl group in the trisac- The foregoing trisaccharide intermediate (III) is then reduced utilizing known techniques, preferably via catalytic hydrogenation utilizing 10% palladium-on-carbon as catalyst to obtain the corresponding N-unprotected-O-protected-5'-amino-trisaccharide followed by basic hydrolysis to obtain a 5'-aminopentofuranosyl-garamine antibacterial agent of this invention (e.g., 4-O-(2,3,5-trideoxy-5-amino-α-D-pentofuranosyl)-6-O-garosaminyl-2-deoxystreptamine which is isolated and purified utilizing known techniques usually including chromatographic techniques.

The 1-N-alkyl compounds of this invention as well as the 5-epi-, 5-deoxy-, 5-epi-amino-5-deoxy-, 5-epi-azido-5-deoxy-, 5-fluoro-5-deoxy-, and 5-epi-fluoro-5-deoxy derivatives are conveniently obtained by starting with disaccharides having the substituent and/or configuration desired in the 5'-amino-α-D-pentofuranosyl trisaccharide antibacterial agent. Alternatively, one may introduce the desired derivatives or configuration into a trisaccharide of this invention utilizing techniques known in the art, such as those described in U.S. Pat. No. 4,002,742 for introduction of a 1-N-alkyl group and in U.S. Pat. Nos. 4,000,261; 4,053,591; 4,000,262 for the preparation of 5-epi-, 5-deoxy-, 5-epi-amino-5-deoxy- and 5-epi-azido-5-deoxy- derivatives, respectively, and in South African Pat. No. 78/0385 for the preparation of 5-epi-fluoro-5-deoxy and 5-fluoro-5-deoxy derivatives.

When preparing the preferred 1-N-(ω-amino-α-hydroxyalkanoyl) derivatives of this invention (e.g., 1-N-(S-β-amino-α-hydroxypropionyl)-[4-O-(2,3,5-trideoxy-5-amino-α-D-pentofuranosyl)-6-O-garosaminyl-2-deoxystreptamine]) it is preferable to first prepare the 1-N-unsubstituted-4-O-(trideoxyaminopentofuranosyl)garamine and then introduce the 1-N-(ω-amino-α-hydroxyalkanoyl)substituent using procedures well known in the art and illustrated in detail in Example 3 herein.

The processes described hereinabove are illustrated in detail hereinbelow in the Preparations and Examples but should not be construed as limiting the scope of my invention, obvious equivalents of which will be apparent to those skilled in the art and which are considered as within the scope of this invention.

METHOD-OF-USE AND PHARMACEUTICAL FORMULATION ASPECTS

The present invention includes within its scope the method of eliciting an antibacterial response in a warm-blooded animal having a susceptible bacterial infection which comprises administering to said animal a non-toxic, antibacterially effective amount of a 4-O-(2,3,5-trideoxy-5-amino-α-D-pentofuranosyl)-6-O-aminoglycosyl-1,3-diaminocyclitol of this invention.

Also included within my invention are pharmaceutical formulations comprising a non-toxic, antibacterially effective amount of a 4-O-(2,3,5-trideoxy-5-amino-α-D-pentofuranosyl)-6-O-aminoglycosyl-1,3-diaminocyclitol of this invention together with a non-toxic, pharmaceutically acceptable carrier.

As discussed hereinabove, the antibacterially effective compounds of my invention and their non-toxic, pharmaceutically acceptable acid addition salts are, in general, broad spectrum antibacterial agents which exhibit activity against both gram-positive and gram-negative bacteria which thus renders them useful for combatting infections in humans or in animals caused by gram-positive bacteria (e.g., *Staphylococcus aureus* and *Bacillus subtilis*) or by gram-negative bacteria (e.g., *Escherichia coli* and *Pseudomonas aeruginosa*). In veterinary applications, my compounds are particularly useful in the treatment of mastitis in cattle and Salmonella induced diarrhea in domestic animals such as the dog and the cat. Additionally, my compounds may be used to disinfect laboratory glassware, dental and medical equipment.

The dosage administered of the novel antibacterial agents of my invention will be dependent upon the age and weight of the animal species being treated, the mode of administration, and the type and severity of bacterial infection being prevented or reduced. In general, the dosage of preferred compound of my invention employed to combat a given bacterial infection will be similar to the dosage requirements of amikacin or 1-N-HAPA-gentamicin B.

The 4-O-(2,3,5-trideoxy-5-amino-α-D-pentofuranosyl)garamines of this invention, preferably the 1-N-(γ-amino-α-hydroxybutyryl)- and the 1-N-(β-amino-α-hyroxypropionyl) derivatives, and the pharmaceutically acceptable acid addition salts thereof may be administered orally, compounded in the form of tablets, capsules, elixirs, or the like or may even be admixed with animal feed. It is in these dosage forms that the antibacterials are most effective for treating bacterial infections of the gastrointestinal tract, which infections cause diarrhea. They are also useful in pre- and post-operative gut sterilization.

My novel antibacterial agents may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, fats, waxes, polyesters, alcohols, polyols and the like.

In general, the topical preparations will contain from about 0.1 to about 3.0 gms. of a 4-0-(2,3,5-trideoxy-5-amino-α-D-pentofuranosyl)-garamine derivative per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 30 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed.

| Tablet | Formulation 1 | | |
|---|---|---|---|
| | 10 mg. Tab. | 25 mg. Tab. | 100 mg. Tab. |
| 1-N-(S-β-amino-α-hydroxy-propionyl)-4-O-(2,3,5-trideoxy-5 -amino-α-D-pento-furanosyl) (1→4) garamine sulfate | 10.5* mg. 95 | 26.25* mg. | 105.0* mg. |
| Lactose, impalpable powder | 197.50 mg. | 171.25 mg. | 126.00 mg. |
| Corn starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of the 1-N-(S-β-amino-α-hydroxypropionyl)-4-O-(2,3,5,-trideoxy-5-amino-α-D-pentofuranosyl)(1→4)garamine sulfate, lactose and polyvinylpyrrrolidone. Spray dry the slurry. Add the corn starch and magnesium stearate. Mix and compress into tablets.

| Formulation 2 | |
|---|---|
| Ointment | |
| 1-N-(S-β-amino-α-hydroxy-propionyl)-4-O-(2,3,5-trideoxy-5-amino-α-D-pentofuranosyl)(1→4)garamine sulfate | 1.9 gm. |
| Methylparaben, USP | 0.5 gm. |
| Propylparaben, USP | 0.1 gm. |
| Petrolatum | to 1000 gm. |

Procedure (1) Melt the petrolatum.

(2) Mix the 1-N-(S-β-amino-α-hydroxypropionyl)-4-O-(2,3,5-trideoxy-5-amino-α-D-pentofuranosyl)(1→4)garamine sulfate, methylparaben and propylparaben with about 10% of the molten petrolatum.

(3) Pass the mixture through a colloid mill.

(4) Add the remainder of the petrolatum with agitation and cool the mixture until it becomes semi-solid. At this stage the product may be put into suitable containers.

Ointments of other 4-O-(2,3,5-trideoxy-5-amino-α-D-pentofuranosyl)garamine derivatives of this invention are prepared by substituting an equivalent quantity of each of said derivatives or an acid addition salt thereof, for 1-N-(S-β-amino-α-hydroxypropionyl)4-O-(2,3,5-trideoxy-5-amino-α-D-pentofuranosyl)(1→4)garamine sulfate in the foregoing formulation.

| | Formulation 3 | |
|---|---|---|
| Injectable Solution | Per 2.0 ml. Vial | Per 50 Liters |
| 1-N-(S-β-amino-α-hydroxy-propionyl)-4-O-(2,3,5-trideoxy-5-amino-α-D-pentofuranosyl)(1→4)garamine sulfate | 84* mgs. | 2100* gms. |
| Methylparaben, USP | 2.6 mgs. | 90.0 gms. |
| Propylparaben, USP | 0.4 mgs. | 10.0 gms. |
| Sodium bisulfite, USP | 4.8 mgs. | 120.0 gms. |
| Sodium sulfite, USP | 1.6 mgs. | 40.0 gms. |
| Disodium Ethylenediamine tetraacetate dihydrate, R.G. | 0.2 mgs. | 5.0 gms. |
| Water, USP q.s. | 2.0 ml. | 50.0 liters |

*Includes a 5% manufacturing overcharge

Procedure: For a 50.0 Liter Batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°-30° C. by circulating cold water through the tank jacket. Sparge the solution with nitrogen gas for at least 10 minutes and keep covered with nitrogen during subsequent processing. Charge and dissolve the disodium EDTA, sodium bisulfite, and sodium sulfite. Charge and dissolve the 1-N-(S-β-amino-α-hydroxypropionyl)-4O-(2,3,5-trideoxy-5-amino-α-D-pentofuranosyl)-(1→4)garamine sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogenfree multiple dose vials, stopper and seal.

In like manner, injectable solutions of other 4-O-(2,3,5-trideoxy-5-amino-α-D-pentofuranosyl)(1→4)garamines and especially acid addition salts of such antibacterial agents, may be prepared by substituting an equivalent quantity of such compounds for 1-N-(S-β-amino-α-hydroxypropionyl)-4-O-(2,3,5-trideoxy-5-amino-α-D-pentofuranosyl)(1→4)garamine sulfate and by following the procedure set forth above.

PREPARATIONS

Preparation 1

S-5-(ETHOXYCARBONYL)-TETRAHYDROFURAN-2-ONE

To a stirred solution of L-glutamic acid (200 gms.) in water (500 ml.) containing sulfuric acid (55 ml.) cooled in ice and water, add over a 90-minute period a solution of sodium nitrite (140 gms.) in water (250 ml.). Allow the solution to warm to room temperature, stir an additional 3 hours, then add a sodium hydroxide solution until the reaction mixture is at pH 2. Evaporate the reaction mixture in vacuo at 60°-70° C. until all the water has been removed. Extract the resultant residue with several 1 liter portions of ethyl acetate until the insoluble salt residue is dry and free-flowing. Dry the combined ethyl acetate extracts over magnesium sulfate, evaporate in vacuo, then heat the resultant residue up to 150° C. first under moderate vacuum, then at vacuums of <1 mm. Continue heating at 150° C. and <1 mm. mercury vacuum for 3 hours to obtain a residue comprising S-5-(carboxytetrahydrofuran)-2-one.

To the residue comprising S-5-carboxytetrahydrofuran-2-one add dry benzene (600 ml.), absolute ethanol (220 ml.) and p-toluenesulfonic acid (0.5 gms.), and heat at reflux temperature with stirring for 1 hour. Distill the reaction mixture through a fractionating column until the azeotropic mixture of benzene: ethanol:water (b.p. 64° C.) is removed and the azeotropic mixture of benzene:ethanol (b.p. 70° C.) begins distilling. Add sodium bicarbonate (0.3 gms.) to the resultant mixture, then evaporate in vacuo followed by distillation in vacuo to obtain S-5-(ethoxycarbonyl)-tetrahydrofuran-2-one, b.p. 95°-100° C./0.25 mm.; $[\alpha]_D^{26}+7.2°$ (chloroform, c=2.2); yield 105 gms., 66% theory.

Preparation 2

S-5-(ETHOXYCARBONYL)-2-HYDROXYTETRAHYDROFURAN

Stir dry sodium borohydride (6.25 gms.) in dry tetrahydrofuran (250 ml.) at 5°-10° C. under an atmosphere of argon and add dropwise borontrifluoride ether complex (28 ml.), followed by a solution of 2-methyl-2-butene (44 ml.) in tetrahydrofuran (40 ml.). Continue stirring the reaction mixture at 5°-10° C. for 1 hour, then slowly add a solution of S-5-(ethoxycarbonyl)tetrahydrofuran-2-one (19 gms.) in tetrahydrofuran (30 ml.), and stir the reaction mixture at room temperature for 18 hours. Add dropwise a solution of water (18 ml.) in tetrahydrofuran (100 ml.) followed by a solution of sodium acetate (40 gms.) and potassium carbonate (5 gms.) in water (120 ml.). Cool the two-phase reaction mixture in an ice bath and stir rapidly while adding dropwise 50% hydrogen peroxide (30 ml.) keeping the internal temperature below 25° C. Continue stirring for 30 minutes, then add ethyl acetate (150 ml.) and filter. Wash the insoluble salts with ethyl acetate, add the ethyl acetate washing to the filtrate, and separate the organic layer. Extract the aqueous layer with tetrahydrofuran:ethyl acetate (4:1 v/v) (400 ml.), then wash the combined organic layers with saturated sodium chloride solution (100 ml.), then filter the combined organic layers rapidly through sodium carbonate powder (anhydrous-50 gms.). Evaporate the solution, then add benzene (2×100 ml. portions) to the resultant residue and evaporate the solvents after each addition. Dissolve the resultant residue in benzene and chromatograph rapidly on silica gel (100 gms.) eluting with increasing portions of ethyl acetate:benzene. Combine the like fractions containing the desired product as determined by thin layer chromatography, and evaporate to a residue comprising S-5-(ethoxycarbonyl)-2-hydroxytetrahydrofuran (12.4 gms.; 64%). Further purify by distillation on a Kugelrohr (b.p. 150°/0.5 mm.) to obtain S-5-(ethoxycarbonyl)-2-hydroxytetrahydrofuran; $\nu_{max}$ (film), 3350, 1735 cm$^{-1}$. Found: C, 52.35; H, 7.5; $C_7H_{12}O_4$ requires C, 52.5; H, 7.55 pmr (CDCl$_3$): δ 1.35 (t, J=7 Hz, 3, ester CH$_3$); ca 2.0 (m, 4, H-2+H-3); 4.26+4.32 (each q, J=7 Hz, total 2, ester CH$_2$); 4.7 (m, 2, H-4+OH), 5.66 and 5.76 (both m; total 1; H-1).

Preparation 3

S-5-(ETHOXYCARBONYL)-2-ETHOXYTETRAHYDROFURAN

To S-5-(ethoxycarbonyl)-2-hydroxytetrahydrofuran (15 gms.) in ethanol (150 ml.) add p-toluenesulfonic acid (0.2 gms.), then evaporate in vacuo at 40° C. to a residue of about 50 ml. Add dry ethanol (150 ml.) and evaporate in vacuo at 40° C. Add benzene (150 ml.) to the resultant residue, then filter through anhydrous powdered sodium carbonate (10 gms.) and evaporate at 40° C. in vacuo to a residue comprising S-5-(ethoxycarbonyl)-2-ethoxytetrahydrofuran. Purify further by distillation on a Kugelrohr, b.p. 70° C./0.2 mm., $\nu_{max}$ (film), 1735 cm.$^{-1}$; Found C, 57.4; H, 8.4; $C_9H_{16}O_4$ req. C, 57.4; H, 8.6%; pmr (CDCl$_3$): δ 1.24 (t, J=7 Hz, 3, aglycone-CH$_3$); 1.33 (t, J=7 Hz, 3, ester CH$_3$); ca 2.0 (m, 4, H-2+H-3) ca 3.5 (m, 2, aglycone-CH$_2$); 4.19 (q, J=7 Hz, 2, ester-CH$_2$); 4.60 (m, 1, H-4) and 5.20, 5.36 (both m, total 1, H-1).

In the above procedure, by substituting for ethanol other lower alkanols such as methanol, propanol, or N-butanol, there is prepared the corresponding 2-alkoxy derivative, e.g., S-5-(ethoxycarbonyl)-2-methoxytetrahydrofuran, S-5-(ethoxycarbonyl)-2-propoxytetrahydrofuran, and S-5-(ethoxycarbonyl)-2-n-butoxytetrahydrofuran, respectively.

Preparation 4

S-5-(AZIDOMETHYL)-2-ETHOXYTETRAHYDROFURAN

A. S-5-(Hydroxymethyl)-2-Ethoxytetrahydrofuran

To a stirred solution of S-5-(ethoxycarbonyl)-2-ethoxytetrahydrofuran (10 gms.) in dry tetrahydrofuran (90 ml.) at 0°-5° C. add dropwise lithium aluminum hydride (1 mol in tetrahydrofuran; 45 ml.). Stir the reaction mixture at room temperature for 1 hour, then slowly add ethyl acetate (18 ml.) followed by ether (200 ml.), then aqueous sodium hydroxide (5% w/v) (8 ml.). Separate the resultant precipitate by filtration and wash with tetrahydrofuran. Evaporate the combined filtrate and tetrahydorfuran washing and dissolve the resultant residue in dry benzene (300 ml.). Evaporate the benzene solution to obtain S-5-(hydroxymethyl)-2-ethoxytetrahydrofuran (yield=6.2 gms.; 79% theory), which is used without further purification in the procedure of Preparation 4B.

B.

S-5-(p-Toluenesulfonyloxymethyl)-2-Ethoxytetrahydrofuran

To a stirred solution of S-5-(hydroxymethyl)-2-ethoxytetrahydrofuran (6.1 gms.) in pyridine (22 ml.) at 0°-5° C. add p-toluenesulfonyl chloride (9.5 gms.). Warm the reaction mixture to room temperature, then continue stirring at room temperature for 4 hours. Dissolve the reaction mixture in chloroform and wash the chloroform solution with dilute hydrochloric acid, water, then sodium bicarbonate solution. Evaporate the organic solution and chromatograph the resultant residue on silica gel eluting with hexane:benzene (1:1). Combine the like eluates containing the desired product as determined by thin layer chromatography and evaporate the combined eluates to a residue comprising an anomeric mixture of S-5-(p-toluenesulfonyloxymethyl)-2-ethoxytetrahydrofuran (10.4 gms.; 84% theory), which is used without further purification in the procedure of Preparation 4C.

C. S-5-(Axidomethyl)-2-Ethoxytetrahydrofuran

Stir a mixture of S-5-(p-toluenesulfonyloxymethyl)-2-ethoxytetrahydrofuran (3 gms.) prepared as described in Preparation 4B, sodium azide (3.25 gms.), water (2 ml.), and dimethylformamide (15 ml.) at 80°-85° C. for 20 hours. Add water to the reaction mixture (100 ml.) and extract with hexane:ether (3:1 v/v) (3×50 ml.). Wash the combined extracts with 100 ml. of water, dry over anhydrous sodium carbonate, filter and evaporate carefully in vacuo at 30° C. until almost all the solvent has been removed. Chromatograph the resultant residue on silica gel (20 gms.) eluting with benzene. Combine the like eluates containing the desired product as determined by thin layer chromatography, remove the benzene by distillation in vacuo, then distill the resultant residue at 60° C. (bath temperature) at 1 mm. pressure to obtain S-5-(azidomethyl)-2-ethoxytetrahydrofuran (yield=1.3 gms.; 75% theory); $\nu_{max}$ (film) 2170 cm$^{-1}$. Found C, 49.2; H, 7.6; N, 24.6. $C_7H_{13}N_3O_2$ req. C, 49.1; H, 7.65; N, 24.5%.

D.

In the procedure of Preparations 4A, B and C, by utilizing as starting compound other 2-alkoxytetrahydrofuran derivatives such as those described in the last paragraph of Preparation 3, there is obtained the corresponding S-5-(azidomethyl)-2-alkoxytetrahydrofuran, i.e., S-5-(azidomethyl)-2-methoxytetrahydrofuran, S-5-(azidomethyl)-2-propoxytetrahydrofuran, and S-5-(azidomethyl)-2-n-butoxytetrahydrofuran.

Preparation 5

4'-Desmethylgaramine and the 4'-epimer thereof

A.

1,3,3'-Tri-N-Benzyloxycarbonyl-4'-Desmethylgaramine (1) To a stirred solution of Antibiotic 66-40D (10 gms.) and powdered anhydrous sodium carbonate (30 gms.) in methanol (300 ml.) and water (30 ml.) at 0°–5° C., add benzylchloroformate (30 ml.) dropwise over a period of one hour. Stir overnight at room temperature, dilute with water (100 ml.), extract with chloroform and evaporate the combined extracts to a residue comprising 1,3,2',6',3''-penta-N-benzyloxycarbonyl-Antibiotic 66-40D, which is used without further purification in the procedure following.

(2) To a solution of the penta-N-benzyloxycarbonyl-Antibiotic 66-40D prepared in Preparation 5A(1) in tetrahydrofuran (500 ml.) and water (20 ml.) add Amberlite IR-120 (H$^⊕$) resin (20 gms.) and stir at room temperature for 24 hours. Filter the reaction mixture, evaporate the filtrate, dissolve the resultant residue in chloroform and chromatograph on silica gel (500 gms.) eluting with 5% methanol in chloroform. Combine the like fractions containing the desired product as determined by thin layer chromatography and evaporate. Dissolve the resulting residue in chloroform (50 ml.) and methanol (5 ml.), and add the solution to a stirred mixture of ether (250 ml.) and hexane (250 ml.). Separate the resultant precipitate by filtration, wash with ether, and dry in vacuo at 50° C. to obtain 1,3,3'-tri-N-benzyloxycarbonyl-4'-desmethylgaramine.

B. 4'-Desmethylgaramine

In a manner similar to that described in Example 1B, hydrogenate 1,3,3'-tri-N-benzyloxycarbonyl-4'-desmethylgaramine in aqueous dioxane at 60 psi in the presence of 10% palladium-on-carbon. Isolate and purify the resultant product in a manner similar to that described to obtain 4'-desmethylgaramine.

C. 4'-Desmethyl-4'-Epigaramine

Subject Antibiotic 66-40B to a series of reactions similar to those described in Preparations 5A and B. Isolate and purify the resultant product in a manner similar to that described to obtain 4'-desmethyl-4'-epigaramine.

Preparation 6

3'-Desmethylgaramine

Prepare a solution containing garamine (7 gms.), iodine (10 gms.) and sodium acetate (20 gms.) in 50% aqueous methanol (250 ml.), and heat at 45°–50° C. for a period of 6 hours, keeping the pH of the solution at 8–9 by adding small quantities of 1 N sodium hydroxide. Continue heating the reaction mixture at 45°–50° C. for an additional 20 hours. Add sodium thiosulfate to the solution until it becomes colorless, then add Amberlite IRC-50 (H$^⊕$) ion exchange resin and stir the mixture until the aminoglycosides are completely adsorbed by the resin. Separate the resin by filtration and wash with water, then elute the washed resin with 2 N ammonium hydroxide. Evaporate the combined eluates and chromatograph the resultant residue on silica gel (200 gms.) eluting with the lower phase of a 1:1:1 chloroform:methanol:28% ammonium hydroxide mixture. Combine the like eluates containing the desired product as determined by thin layer chromatography and evaporate. Dissolve the resultant residue in water, and pass the aqueous solution through a short column of IRA-401S (OH$^⊖$) resin eluting with water. Lyophilize the combined eluates to a residue comprising 3'-desmethylgaramine.

Preparation 7

3',4'-Desmethylgaramine and the 4'-epimer thereof

Treat each of 4'-desmethylgaramine and 4'-desmethyl-4'-epigaramine with iodine and sodium acetate in 50% aqueous methanol in a manner similar to that described in Preparation 6 and isolate and purify each of the resultant products in a manner similar to that described to obtain, respectively, 3',4'-desmethylgaramine and 3',4'-desmethyl-4'-epigaramine.

Preparation 8

1,3,3'-Tri-N-benzyloxycarbonyl-5,2',4'-tri-O-acetyl-derivatives of 3'-desmethylgaramine, 4'-desmethylgaramine, 4'-desmethyl-4'-epigaramine, 3',4'-bisdesmethylgaramine and 3',4'-bisdesmethyl-4'-epigaramine A. Utilizing procedures known in the art (such as described in U.S. Pat. No. 4,063,015) treat 3'-desmethylgaramine with sodium carbonate and carbobenzyloxy chloride in water to obtain 1,3,3'-tri-N-benzyloxycarbonyl-3'-desmethylgaramine. Treat the foregoing with (2,2,2-trichloroethyl)chloroformate in dry pyridine to obtain 1,3,3'-tri-N-benzyloxycarbonyl-4-O-(2,2,2-trichloroethylcarbonyl)-3'-desmethylgaramine; treatment thereof with acetic acid in the presence of trifluoroacetic anhydride and p-toluenesulfonic acid yields 1,3,3'-tri-N-benzyloxycarbonyl-4-O-(2,2,2-trichloroethylcarbonyl)-5,2',4'-tri-O-acetyl-3'-desmethylgaramine. Reaction of the foregoing with zinc in acetic acid yields 1,3,3'-tri-N-benzyloxycarbonyl-5,2',4'-tri-O-acetyl-3'-desmethylgaramine.

B. Treat each of the compounds prepared as described in Preparations 5B, 6 and 7 in a manner similar to that described in Preparation 8A to obtain, respectively, 1,3,3'-tri-N-benzyloxycarbonyl-5,2',4'-tri-O-acetyl-4'-desmethylgaramine, 1,3,3'-tri-N-benzyloxycarbonyl-5,2',4'-tri-O-acetyl-4'-desmethyl-4'-epigaramine, 1,3,3'-tri-N-benzyloxycarbonyl-5,2',4'-tri-O-acetyl-3',4'-bisdesmethylgaramine and 1,3,3'-tri-N-benzyloxycarbonyl-5,2',4'-tri-O-acetyl-3',4'-bisdesmethyl-4'-epigaramine.

EXAMPLES

Example 1

4-O-(2,3,5-Trideoxy-5-amino-α-D-pentofuranosyl)-6-O-garosaminyl-2-deoxystreptamine

A.

1,3,3''-Tri-N-Benzyloxycarbonyl-5,2'',4''-Tri-O-Acetyl-[4-O-(2,3,5-Trideoxy-5-Azido-α-D-Pentofuranosyl)-6-O-Garosaminyl-2-Deoxystreptamine]

(1) Prepare a mixture of S-5-(azidomethyl)-2-ethoxytetrahydrofuran (1.1 gms.), dry benzene (25 ml.), p-toluenesulfonic acid (10 mg.), and 1,3,3'-tri-N-benzyloxycarbonyl-5,2',4'-tri-O-acetylgaramine (5.46 gms.), then stir and heat the mixture for slow distillation of benzene, maintaining the reaction mixture volume by addition of dry benzene. Continue for 2 hours, then cool the reaction mixture and stir with a small amount of IRA-401S (OH$^⊖$) resin until the reaction mixture is neutral. Filter the reaction mixture, evaporate the filtrate, and chromatograph the resultant residue on silica gel (300 gms.) eluting with chloroform. Combine the like eluates containing the desired product as determined by thin layer chromatography and evaporate to a residue comprising 1,3,3''-tri-N-benzyloxycarbonyl-5,2'',4''-tri-O-acetyl-[4-

O-(2,3,5-trideoxy-5-azido-α-D-pentofuranosyl)-6-O-garosaminyl-2-deoxystreptamine]. Purify by dissolving the residue in dichloromethane (15 ml.) and adding this solution dropwise to stirred hexane (200 ml.). Filter the resultant precipitate and dry to give an amorphous white powder (yield 4.01 gms., 63% theory); m.p. 100°–105° C.; $[\alpha]_D^{26} + 106.1°$ (chloroform, c=0.8). Found: C, 58.5; H, 6.0; N, 8.4 $C_{48}H_{58}N_6O_{16}.0.5H_2O$ requires C, 58.6; H, 6.0; N, 8.5%.

(2) In the foregoing procedure, instead of S-5-(azidomethyl)-2-ethoxytetrahydrofuran, there may be used as reagent equivalent quantities of other S-5-(azidomethyl)-2-alkoxytetrahydrofurans such as those described in Preparation 4D.

B.
4-O-(2,3,5-Trideoxy-5-Amino-α-D-Pentofuranosyl)-6-O-Garosaminyl-2-Deoxystreptamine Prepare a solution of 1,3,3″-tri-N-benzyloxycarbonyl-5,2″,4″-tri-O-acetyl-[4-O-(2,3,5-trideoxy-5-azido-α-D-pentofuranosyl)-6-O-garosaminyl-2-deoxystreptamine] (1.0 gm.) in dioxane (20 ml.) and water (10 ml.) and hydrogenate for 20 hours at 60 psi hydrogen in the presence of 10% palladium-on-carbon (0.5 gms.). Separate the catalyst by filtration and wash with dioxane (50 ml.), then with aqueous ammonia (1 N; 100 ml.) and evaporate the combined filtrate and washings to a foamy residue. To this residue add aqueous sodium hydroxide (2 N; 10 ml.) and heat under an atmosphere of argon at 100°–110° C. for 2 days. Cool the reaction mixture and carefully add hydrochloric acid (1 N) until the reaction mixture is at a pH of about 9. Evaporate the reaction mixture and extract the resultant residue with several portions of dry ethanol until thin layer chromatography of a portion of the residue indicates the absence of aminoglycoside. Evaporate the combined extracts and chromatograph the resultant residue on silica gel eluting with the lower phase of a chloroform:methanol:10% ammonium hydroxide (v/v/v) mixture. Again combine the like eluates containing the desired product as determined by thin layer chromatography and evaporate and dissolve the resultant residue in water. Pass the aqueous solution through a short column of IRA-401S (OH⊖) resin eluting with water. Collect the eluates under an atmosphere of nitrogen and lyophilize to a residue of 4-O-(2,3,5-trideoxy-5-amino-α-D-pentofuranosyl)-6-O-garosaminyl-2-deoxystreptamine (yield 0.23 gms.; 54% theory); m.p. 59°–65° C.; $[\alpha]_D^{26} + 175.2°$ (H₂O, c=0.4); Found: C, 50.6; H, 9.0; N, 12.8. $C_{18}H_{36}N_4O_7.0.5H_2O$ requires C, 50.3; H, 8.6; N, 13.05%. Mass spectrum: m/e 421, 390, 322, 304, 289, 229, 191, 173, 163, 160, 130 and 100; pmr (D₂O): δ1.17 (s, 3, 4‴-CH₃); 2.48 (s, 3, NCH₃); 2.51 (d, $J_{2″,3″}=11$ Hz, 1, H-3″); 2.68 (d, $J_{4′,5′}=6$ Hz, 2, H-5′); 3.76 (dd, $J_{2″,3″}=11$ Hz, $J_{1″,2″}=4$ Hz, 1, H-2″); 4.00 (d, $J_{5″eq5″ax}=12.5$ Hz, 1, H-5eq); 4.23 (m, 1, H-4′); 5.03 (d, $J_{1″,2″}=4$ Hz, 1, H-1″) and 5.51 (m, 1, H-1′).

EXAMPLE 2

3′- and/or 4′-desmethyl derivatives of 4-O-(2,3,5-trideoxy-5-amino-α-D-pentofuranosyl)-6-O-garosaminyl-2-deoxystreptamine A. In a manner similar to that described in Example 1A, treat each of the following blocked garamine derivatives with S-5-(azidomethyl)-2-ethoxytetrahydrofuran in benzene in the presence of p-toluenesulfonic acid:

(1) 1,3,3′-tri-N-benzyloxycarbonyl-5,2′,4′-tri-O-acetyl-3′-desmethylgaramine,
(2) 1,3,3′-tri-N-benzyloxycarbonyl-5,2′,4′-tri-O-acetyl-4′-desmethylgaramine,
(3) 1,3,3′-tri-N-benzyloxycarbonyl-5,2′,4′-tri-O-acetyl-4′-desmethyl-4′-epi-garamine,
(4) 1,3,3′-tri-N-benzyloxycarbonyl-5,2′,4′-tri-O-acetyl-3′,4′-bisdesmethylgaramine,
(5) 1,3,3′-tri-N-benzyloxycarbonyl-5,2′,4′-tri-O-acetyl-3′,4′-bisdesmethyl-4′-epi-garamine.

Isolate and purify each of the resultant products in a manner similar to that described in Example 1A to obtain, respectively,
(1) 1,3,3″-tri-N-benzyloxycarbonyl-5,2″,4″-tri-O-acetyl-[4-O-(2,3,5-trideoxy-5-azido-α-D-pentofuranosyl)-6-O-(3-desmethylgarosaminyl)-2-deoxystreptamine],
(2) 1,3,3″-tri-N-benzyloxycarbonyl-5,2″,4″-tri-O-acetyl-[4-O-(2,3,5-trideoxy-5-azido-α-D-pentofuranosyl)-6-O-(4-desmethylgarosaminyl)-2-deoxystreptamine],
(3) 1,3,3″-tri-N-benzyloxycarbonyl-5,2″,4″-tri-O-acetyl-[4-O-(2,3,5-trideoxy-5-azido-α-D-pentofuranosyl)-6-O-(4-desmethyl-4-epi-garosaminyl)-2-deoxystreptamine],
(4) 1,3,3″-tri-N-benzyloxycarbonyl-5,2″,4″-tri-O-acetyl-[4-O-(2,3,5-trideoxy-5-azido-α-D-pentofuranosyl)-6-O-(3,4-bisdesmethylgarosaminyl)-2-deoxystrepamine],
(5) 1,3,3″-tri-N-benzyloxycarbonyl-5,2″,4″-tri-O-acetyl-[4-O-(2,3,5-trideoxy-5-azido-α-D-pentofuranosyl)-6-O-(3,4-bisdesmethyl-4-epi-garosaminyl)-2-deoxystreptamine].

B. Hydrogenate each of the 5′-azido derivatives prepared in above Example 2A followed by removal of the blocking groups by reaction with aqueous sodium hydroxide and then hydrochloric acid in a manner similar to that described in Example 1B. Isolate and purify each of the resultant products in a manner similar to that described to obtain, respectively,
(1) 4-O-(2,3,5-trideoxy-5-amino-α-D-pentofuranosyl)-6-O-(3-desmethylgarosaminyl)-2-deoxystreptamine,
(2) 4-O-(2,3,5-trideoxy-5-amino-α-D-pentofuranosyl)-6-O-(4-desmethylgarosaminyl)-2-deoxystreptamine,
(3) 4-O-(2,3,5-trideoxy-5-amino-α-D-pentofuranosyl)-6-O-(4-desmethyl-4-epi-garosaminyl)-2-deoxystreptamine,
(4) 4-O-(2,3,5-trideoxy-5-amino-α-D-pentofuranosyl)-6-O-(3,4-bisdesmethylgarosaminyl)-2-deoxystrepamine,
(5) 4-O-(2,3,5-trideoxy-5-amino-α-D-pentofuranosyl)-6-O-(3,4-bisdesmethyl-4-epi-garosaminyl)-2-deoxystreptamine.

EXAMPLE 3

1-N-(ω-amino-α-hydroxyalkanoyl)-[4-(2,3,5-trideoxy-5-amino-α-D-pentofuranosyl)-6-O-garosaminyl-2-deoxystreptamines]

A.
3,5′-Di-N-Benzyloxycarbonyl-[4-O-(2,3,5-Trideoxy-5-Amino-α-D-Pentofuranosyl)-6-O-Garosaminyl-2-Deoxystreptamine]

To a solution of 4-O-(2,3,5-trideoxy-5-amino-α-D-pentofuranosyl)-6-O-garosaminyl-2-deoxystreptamine (0.84 gms.) in dimethylsulfoxide (40 ml.), add powdered nickel (II) acetate (1.02 gms.) and powdered copper (II) acetate (0.8 gms.) and stir at room temperature for 30 minutes. Add a solution of N-(benzyloxycarbonyloxy)phthalimide (1.22 gms.) in chloroform (8 ml.), stir the reaction mixture for 30 minutes, then pour into a solution of sodium chloride (80 gm.) in 3 N ammonium hydroxide solution (400 ml.), and extract with chloroform (3×100 ml.). Wash the combined extracts with a solution of sodium chloride in ammonium hydroxide (20 gms. sodium chloride per 100 ml. of 3 N ammonium hydroxide). Dry the chloroform extracts over potassium carbonate and evaporate to a residue comprising 3,5'-di-N-benzyloxycarbonyl-[4-O-(2,3,5-trideoxy-5-amino-α-D-pentofuranosyl)-6-O-garosaminyl-2-deoxystreptamine]. Purify by chromatographing on 15 gms. silica gel eluting with 10:1:0.5 (v/v/v) chloroform:methanol:concentrated ammonium hydroxide. Combine the like eluates containing the desired product as determined by thin layer chromatography and evaporate and dry the resultant residue in vacuo at 0.1 mm./50° C. to give the 3,5'-di-N-benzyloxycarbonyl-[4-O-2,3,5-trideoxy-5-amino-α-D-pentofuranosyl)-6-O-garosaminyl-2-deoxystreptamine], yield 1.1 gm., 81% theory; $[\alpha]_D^{26}+97.1°$ (chloroform, c=0.2); Found: C, 57.6; H, 6.9; N, 7.9. $C_{34}H_{48}N_4O_{11}.H_2O$ req. C, 57.8; H, 7.1; N, 7.9%.

B.
N-(ω-Benzyloxycarbonylamino-α-Hydroxyalkanoyloxy)Succinimide (1) N-(S-β-Benzyloxycarbonylamino-α-Hydroxypropionyloxy)Succinimide To a solution of S-(β-benzyloxycarbonylamino)-α-hydroxypropionic acid (10 mmol) and dry N-hydroxysuccinimide (10 mmol) in dry dichloromethane (20 ml.) cooled in an ice bath, add dropwise a solution of N,N-dicyclohexylcarbodiimide (10.3 mmol) in dichloromethane (10 ml.). Stir the mixture for 20 hours at room temperature with the exclusion of moisture. Filter the reaction mixture and wash the insolubles with benzene (50 ml.). Evaporate the combined filtrate and benzene washings in vacuo to a volume of about 25 ml. Remove additional precipitate by filtration, wash with benzene and evaporate the combined filtrate and benzene washings in vacuo, dry the resultant residue to a white foam at 0.1 mm. Hg pressure to obtain N-(S-β-benzyloxycarbonylamino)-α-hydroxypropionyloxy)-succinimide, which is used without further purification in the procedure of Example 3C.

(2)
In the procedure of Example 3B(1), substitute for S-(β-benzyloxycarbonylamino)-α-hydroxypropionic acid equivalent amounts of each of the following:
(1) R-(β-benzyloxycarbonylamino)-α-hydroxypropionic acid,
(2) S-(γ-benzyloxycarbonylamino)-α-hydroxybutyric acid,
(3) R-(γ-benzyloxycarbonylamino)-α-hydroxybutyric acid,
(4) S-(δ-benzyloxycarbonylamino)-α-hydroxyvaleric acid,
(5) R-(δ-benzyloxycarbonylamino)-α-hydroxyvaleric acid.

Isolate and purify each of the resultant products in a manner similar to that described to obtain, respectively,
(1) N-(R-β-benzyloxycarbonylamino-α-hydroxypropionyloxy)succinimide,
(2) N-(S-γ-benzyloxycarbonylamino-α-hydroxybutyryloxy)succinimide,
(3) N-(R-γ-benzyloxycarbonylamino-α-hydroxybutyryloxy)succinimide,
(4) N-(S-δ-benzyloxycarbonylamino-α-hydroxyvaleryloxy)succinimide,
(5) N-(R-δ-benzyloxycarbonylamino-α-hydroxyvaleryloxy)succinimide.

C.
1-N-(S-β-Amino-α-Hydroxypropionyl)-[4-O-(2,3,5-Trideoxy-5-Amino-α-D-Pentofuranosyl)-6-O-Garosaminyl-2-Deoxystreptamine]

(1) 1-N-(S-β-Benzyloxycarbonylamino-α-Hydroxypropionyl)-3,5'-Di-N-Benzyloxycarbonyl-[4-O-(2,3,5-Trideoxy-5-Aminopentofuranosyl)-6-O-Garosaminyl-2-Deoxystreptamine]

To a stirred solution of 3,5'-di-N-benzyloxycarbonyl-[4-O-(2,3,5-trideoxy-5-aminopentofuranosyl)-6-O-garosaminyl-2-deoxystreptamine] (1.02 gms.) in dichloromethane (15 ml.), methanol (1 ml.) and triethylamine (0.2 ml.) add dropwise over a period of five minutes a solution of N-(S-β-benzyloxycarbonylamino-α-hydroxypropionyl)succinimide (0.5 gms.) in dichloromethane (3 ml.). Continue stirring at room temperature for 1 hour, then add dropwise another solution of N-(S-β-benzyloxycarbonylamino-α-hydroxypropionyl)succinimide (0.33 gms.) in dichloromethane (2 ml.). Continue stirring for 1.5 hours, then add ethyl acetate (100 ml.) to the reaction mixture. Wash the ethyl acetate solution with 20% aqueous sodium hydroxide, then dry the organic phase over magnesium sulfate, filter and evaporate. Chromatograph the resultant residue on silica gel (20 gms.) eluting with a solvent mixture comprising chloroform:methanol:concentrated ammonium hydroxide (10:1:0.1) (v/v/v). Combine the like fractions containing the desired product as determined by thin layer chromatography and evaporate to a white foamy residue comprising 1-N-(β-benzyloxycarbonylamino-α-hydroxypropionyl)-3,5'-di-N-benzyloxycarbonyl-[4-O-(2,3,5-trideoxy-5-amino-α-D-pentofuranosyl)-6-O-garosaminyl-2-deoxystreptamine], yield 0.74 gms., 57% theory, which is used without further purification in the procedure immediately following.

(2) Add liquid ammonia (redistilled, 30 ml.) to a stirred solution of 1-N-(β-benzyloxycarbonylamino-α-hydroxypropionyl)-3,5'-di-N-benzyloxycarbonyl-[4-O-(2,3,5-trideoxy-5-amino-α-D-pentofuranosyl)-6-O-garosaminyl-2-deoxystreptamine] (0.82 gms.) in tetrahydrofuran (5 ml.), then add sodium metal (0.5 gms.). Stir the reaction mixture for 5 minutes, add ammonium chloride (1.37 gms.), then stir the reaction mixture for another 15 minutes and dilute with water (10 ml.). Evaporate the solution in vacuo and extract the resultant residue with ethanol until thin layer chromatography of a portion of the residue indicates the absence of aminoglycoside. Evaporate the combined ethanol extracts and chromatograph the resultant residue on silica gel eluting with the lower phase of a 1:1:1 (v/v/v) chloroform:methanol:15% ammonia mixture. Combine the like eluates containing the desired product as determined by thin layer chromatography and evaporate. Dissolve the resultant residue in water and pour through a small column of IRA-401S (OH⊖) and elute with water. Collect the eluates under an atmosphere of nitrogen and lyophilize to give 1-N-(S-β-amino-α-hydroxypropionyl)-[4-O-(2,3,5-trideoxy-5-amino-α-D-pentofuranosyl)-6-O-garosaminyl-2-deoxystreptamine] as an amorphous hygroscopic solid, yield 0.18 gms., 33% theory; $[\alpha]_D^{26}+123.2°$ (H$_2$O, c=0.25), pmr (D$_2$O) δ1.17 (s, 3, 4"-CH$_3$); 2.46 (s, 3, NCH$_3$); 2.48 (d, $J_{2'',3''}$=11.5 Hz, 3, H-3"); 2.68 (d, $J_{4',5'}$=6 Hz, 2, H-5');

2.91 (m, 2, H-3'''); 5.06 (d, J₂'',₁''=4 Hz, 1 H-1'') and 5.57 (m, 1, H-1').

D. In the procedure of Example 3C, by substituting for N-(S-β-benzyloxycarbonylamino-α-hydroxypropionyl)succinimide equivalent quantities of each of the products of Example 3B(2), there is obtained, respectively, (1) 1-N-(R-β-amino-α-hydroxyprionyl)-[4-O-(2,3,5-trideoxy-5-amino-α-D-pentofuranosyl)-6-O-garosaminyl-2-deoxystreptamine], (2) 1-N-(S-γ-amino-α-hydroxybutyryl)-[4-O-(2,3,5-trideoxy-5-amino-α-D-pentofuranosyl)-6-O-garosaminyl-2-deoxystreptamine], (3) 1-N-(R-γ-amino-α-hydroxybutyryl)-[4-O-(2,3,5-trideoxy-5-amino-α-D-pentofuranosyl)-6-O-garosaminyl-2-deoxystreptamine], (4) 1-N-(S-δ-amino-α-hydroxyvaleryl)-[4-O-(2,3,5-trideoxy-5-amino-α-D-pentofuranosyl)-6-O-garosaminyl-2-deoxystreptamine], (5) 1-N-(R-δ-amino-α-hydroxyvaleryl)-[4-O-(2,3,5-trideoxy-5-amino-α-D-pentofuranosyl)-6-O-garosaminyl-2-deoxystreptamine].

EXAMPLE 4

3''-And/or 4''-desmethyl derivatives of 1-N-(S-β-amino-α-hydroxypropionyl)-[4-O-(2,3,5-trideoxy-5-amino-α-D-pentofuranosyl)-6-O-garosaminyl-2-deoxystreptamine]

A. In a manner similar to that described in Example 3A, treat each of the products of Example 2B in dimethylsulfoxide with nickel acetate and copper acetate followed by treatment with N-(benzyloxycarbonyloxy)phthalimide and thence ammonium hydroxide. Isolate and purify each of the resultant products in a manner similar to that described in Example 3A to obtain, respectively, the 3,5'-di-N-benzyloxycarbonyl derivative of each of the products of Example 2B.

B. Treat each of the 3,5'-di-N-benzyloxycarbonyl derivatives prepared in Example 4A with N-(S-β-benzyloxycarbonylamino-α-hydroxypropionyl)succinimide followed by treatment of each of the resulting products with sodium in liquid ammonia, thence isolate the resultant products in a manner similar to that described in Example 3C, to obtain, respectively, 1-N-(S-β-amino-α-hydroxypropionyl)-[4-O-(2,3,5-trideoxy-5-amino-α-D-pentofuranosyl)-6-O-(3-desmethyl-garosaminyl)-2-deoxystreptamine]; 1-N-(S-β-amino-α-hydroxypropionyl)-[4-O-(2,3,5-trideoxy-5-amino-α-D-pentofuranosyl)-6-O-(4-desmethylgarosaminyl)-2-deoxystreptamine]; 1-N-(S-β-amino-α-hydroxypropionyl)-[4-O-(2,3,5-trideoxy-5-amino-α-D-pentofuranosyl)-6-O-(4-desmethyl-4-epi-garosaminyl)-2-deoxystreptamine]; 1-N-(S-β-amino-α-hydroxypropionyl)-[4-O-(2,3,5-trideoxy-5-amino-α-D-pentofuranosyl)-6-O-(3,4-bisdesmethylgarosaminyl)-2-deoxystreptamine]; 1-N-(S-β-amino-α-hydroxypropionyl)-[4-O-(2,3,5-trideoxy-5-amino-α-D-pentofuranosyl)-6-O-(3,4-bisdesmethyl-4-epigarosaminyl)-2-deoxystreptamine].

EXAMPLE 5

1-N-Acetyl-[4-O-(2,3,5-trideoxy-5-amino-α-D-pentofuranosyl)-6-O-garosaminyl-2-deoxystreptamine]

(1) To a stirred solution of 3,5'-di-N-benzyloxycarbonyl-[4-O-(2,3,5-trideoxy-5-amino-α-D-pentofuranosyl)-6-O-garosaminyl-2-deoxystreptamine] (0.8 mmol; 0.55 gms.) in methanol (5 ml.) and dichloromethane (5 ml.) at room temperature, add dropwise over a 15-minute period a solution of N-acetoxysuccinimide (1 mmol, 0.15 gms.) in dichloromethane (3 ml.). Stir the reaction mixture for 20 hours at room temperature, add dichloromethane (50 ml.) and wash the reaction solution with 1 N ammonium hydroxide (20 ml.). Separate the layers and dry the organic phase over magnesium sulfate, filter and evaporate to a residue comprising 1-N-acetyl-3,5'-di-N-benzyloxycarbonyl-[4-O-(2,3,5-trideoxy-5-amino-α-D-pentofuranosyl)-6-O-garosaminyl-2-deoxystreptamine].

(2) Dissolve the residue obtained as described in Paragraph 1 in dry tetrahydrofuran (3 ml.), add liquid ammonia (20 ml.), and while stirring this mixture add sodium metal (0.5 gms.) in small portions. Stir the resulting blue solution for 5 minutes, then add ammonium chloride (1.37 gms.) portionwise. When the blue color disappears, dilute the reaction mixture with methanol (5 ml.) and water (10 ml.) and evaporate in vacuo. Extract the resultant residue with ethanol until no additional aminoglycoside is extracted as determined by thin layer chromatography. Evaporate the combined ethanol extracts and chromatograph the resultant residue on silica gel (20 gms.) eluting with the lower phase of a 2:1:1 (v/v/v) chloroform:methanol:10% ammonium hydroxide mixture. Combine the like fractions containing the desired product as determined by thin layer chromatography and evaporate. Dissolve the resultant residue in water and pass through a small column of Amberlite IRA-401S (OH⊖) eluting with water. Lyophilize the combined eluates to a residue comprising 1-N-acetyl-[4-O-(2,3,5-trideoxy-5-amino-α-D-pentofuranosyl)-6-O-garosaminyl-2-deoxystreptamine], yield 0.14 gms., 38% theory; Mass Spectrum m/e 463 (MH+) 432, 233, 205, 187, 160, 100.

EXAMPLE 6

1-N-ethyl-[4O-(2,3,5-trideoxy-5-amino-α-D-pentofuranosyl)6-O-garosaminyl-2-deoxystreptamine]

A. To a stirred solution of 4-O-(2,3,5-trideoxy-5-amino-α-D-pentofuranosyl)-6-O-garosaminyl-2-deoxystreptamine (0.315 gms.) in dimethylsulfoxide (15 ml.) add powdered cupric acetate (0.30 gms.) and nickel (II) acetate (0.37 gms.), and continue stirring for 30 minutes. Add dropwise a solution of acetic anhydride (2.0 eq., 0.15 ml.) in dry tetrahydrofuran (3 ml.) and stir the reaction mixture for 30 minutes at room temperature. Pass hydrogen sulfide into the methanol solution (400 ml.), continue stirring for 1 hour, decant the ethereal solution, rinse the resulting semi-solid residue with ether, discard the ether rinse, and dissolve the resultant residue in methanol (20 ml.). Add hydrogen sulfide to the methanol solution until no further precipitation occurs. Separate the resulting insoluble metal sulfides by filtration and wash thoroughly with methanol. Evaporate the combined filtrate and methanol washings, then co-evaporate with water. Dissolve the resultant residue in water, and pass through a short column of IRA-401S (OH⊖) resin eluting with water. Lyophilize the combined eluates to a residue comprising 3,5'-di-N-acetyl-[4-O-(2,3,5-trideoxy-5-amino-α-D-pentofuranosyl)-6-O-garosaminyl-2-deoxystreptamine] which is used without further purification in the procedure of Example 6B.

B. Dissolve the product of Example 6A in water (5 ml.) containing sodium cyanoborohydride (0.1 gms.), adjust the solution pH to 5.0 by adding 1 N sulfuric acid, then add acetaldehyde (0.05 ml.) and stir the solution at room temperature adding sulfuric acid as needed to maintain pH equal to 5.0. When the alkylation is complete as determined by thin layer chromatography, bring the solution to a pH>8 by adding ammonia, then evaporate to a residue comprising 1-N-ethyl-3,5'-di-N-acetyl-[4-O-(2,3,5-trideoxy-5-amino-α-D-pentofuranosyl)-6-O-garosaminyl-2-deoxystreptamine].

Add a solution of sodium hydroxide (1 gm.) in water (8 ml.) to the foregoing residue and heat for 2 days under an atmosphere of nitrogen at 100°-120° C.; cool, then add dilute hydrochloric acid until the solution is at a pH equal to 9. Evaporate the reaction solution and extract the resultant residue with warm ethanol until the extracts no longer contain aminoglycoside. Evaporate the combined extracts and chromatograph the resultant residue on silica gel eluting with the lower phase of a 2:1:1 (v/v/v) chloroform:methanol:10% ammonium hydroxide mixture. Combine the like fractions containing the desired product as determined by thin layer chromatography and evaporate. Dissolve the resultant residue in water, pass through a small column of IRA-401S (OH⊖) resin eluting with water. Lyophilize the combined eluates to obtain 1-N-ethyl-3,5'-di-N-acetyl-[4-O-(2,3,5-trideoxy-5-amino-α-D-pentofuranosyl)-6-O-garosaminyl-2-deoxystreptamine], yield 0.09 gms. (25% theory); pmr (D₂O): δ 1.19 (s, 3, 4"-CH₃); 1.06 (t, J=7 Hz, CH₂CH₃); 2.50 (s, 3, NCH₃); 2.52 (d, J₂",₃"=11 Hz, 1, H-3"); 2.70 (d, J₄',₅'=6 Hz, 2, H-5'); 3.80 (dd, J₂",₃"=11 Hz, J₁",₂"=4 Hz, 1, H-2"); 4.03 (d, H₅"ax-5"eq=12.5 Hz, 1, H-5"eq); 4.24 (m, 1, H-4'); 4.96 (d, H₁",₂"=4 Hz, 1, H-1") and 5.53 (br. d, 1, H-1'); Mass spectrum m/e 449 (MH+), 418, 350, 322, 318, 317, 259, 229, 219, 201, 191, 173, 160, 130, 100.

EXAMPLE 7

Acid Addition Salts

A. Sulfate Salts (Sulfuric Acid Addition Salts)

Dissolve 5 gms. of 1-N-(β-amino-α-hydroxypropionyl)-[4-O-(2,3,5-trideoxy-5-amino-α-D-pentofuranosyl)-6-O-garosaminyl-2-deoxystreptamine] in 25 ml. of water and adjust the pH of the solution to 4.5 with 1 N sulfuric acid. Pour into about 300 ml. of methanol with vigorous agitation, continue the agitation for about 10-20 minutes and filter. Wash the precipitate with methanol and dry at about 60° C. in vacuo to obtain 1-N-(β-amino-α-hydroxypropionyl)-[4-O-(2,3,5-trideoxy-5-amino-α-D-pentofuranosyl)-6-O-garosaminyl-2-deoxystreptamine] sulfate.

In like manner, the sulfate salts of Examples 1-6 are prepared.

B. Hydrochloride Salts (Hydrochloric Acid Addition Salts)

Dissolve 5 gms. of 1-N-(β-amino-α-hydroxypropionyl)-4-O-(2,3,5-trideoxy-5-amino-α-D-pentofuranosyl)-6-O-garosaminyl-2-deoxystreptamine in 25 ml. of water. Acidify with 2 N hydrochloric acid to pH 5. Lyophilize to obtain 1-N-(β-amino-α-hydroxypropionyl)-[4-O-(2,3,5-trideoxy-5-amino-α-D-pentofuranosyl)-6-O-garosaminyl-2-deoxystreptamine] hydrochloride.

In like manner, the hydrochloride salts of Examples 1-6 are prepared.

I claim:

1. A 4-O-(2,3,5-trideoxy-5-amino-α-D-pentofuranosyl)-6-O-aminoglycosyl-1,3-diaminocyclitol wherein said 6-O-aminoglycosyl is a member selected from the group consisting of garosaminyl, 3-desmethylgarosaminyl, 4-desmethylgarosaminyl, 4-desmethyl-4-epigarosaminyl, 3,4-bisdesmethylgarosaminyl, and 3,4-bisdesmethyl-4-epigarosaminyl, and wherein said 1,3-diaminocyclitol is 2-deoxystreptamine or a 5-epi-, 5-deoxy-, 5-fluoro-5-deoxy-, 5-epi-fluoro-5-deoxy-, 5-epi-azido-5-deoxy-, or a 5-epi-amino-5-deoxy- derivative thereof;

and the 1-N-substituted derivatives thereof wherein said substituent is -CH₂X or

wherein X is a member selected from the group consisting of hydrogen, alkyl, alkenyl, cycloalkyl, cycloalkylalkyl, hydroxyalkyl, aminoalkyl, N-alkylaminoalkyl, aminohydroxyalkyl, N-alkylaminohydroxyalkyl, phenyl, benzyl, and tolyl, said substituent having up to 8 carbon atoms, and when substituted by both amino and hydroxyl groups, bearing said groups on different carbon atoms;

and the pharmaceutically acceptable acid addition salts thereof.

2. A compound of claim 1 which is 4-O-(2,3,5-trideoxy-5-amino-α-D-pentofuranosyl)-6-O-garosaminyl-2-deoxystreptamine and the 5-epi-, 5-deoxy-, 5-fluoro-5-deoxy-, 5-epi-fluoro-5-deoxy-, 5-epi-azido-5-deoxy- and 5-epi-amino-5-deoxy derivatives thereof, the 1-N-CH₂X and the

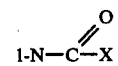

derivatives of the foregoing wherein X is as defined in claim 1, and the pharmaceutically acceptable acid addition salts thereof.

3. A compound of claim 2 which is 4-O-(2,3,5-trideoxy-5-amino-α-D-pentofuranosyl)-6-O-garosaminyl-2-deoxystreptamine.

4. A compound of claim 2 which is 1-N-(ω-amino-α-hydroxyalkanoyl)-[4-O-(2,3,5-trideoxy-5-amino-α-D-pentofuranosyl)-6-O-garosaminyl-2-deoxystreptamine] wherein said alkanoyl has 3 to 5 carbon atoms.

5. A compound of claim 4 which is 1-N-(S-β-amino-α-hydroxypropionyl)-[4-O-(2,3,5-trideoxy-5-amino-α-D-pentofuraosyl)-6-O-garosaminyl-2-deoxystreptamine].

6. The process for the preparation of a 4-O-(2,3,5-trideoxy-5-amino-α-D-pentofuranosyl)-6-O-(aminoglycosyl)-1,3-diaminocyclitol of claim 1;

which comprises the reaction of an N-protected-O-protected-6-O-aminoglycosyl-2-deoxystreptamine having an unprotected-4-hydroxyl group or a 5-epi-, 5-deoxy-, 5-fluoro-5-deoxy-, 5-epi-fluoro-5-deoxy-, 5-epi-azido-5-deoxy- or a 5-epi-N-protected-amino-5-deoxy- derivative thereof, wherein said 6-O-aminoglycosyl is a member selected from the group consisting of garosaminyl, 3-desmethylgarosaminyl, 4-desmethylgarosaminyl, 4-desmethyl-4-epigarosaminyl, 3,4-desmethylgarosaminyl, and 3,4-desmethyl-4-epigarosaminyl, said N- and O-protecting groups being stable to acid and removable by treatment with base;

with a lactol derivative selected from the group consisting of an S-5-(azidomethyl)-2-lower alkoxytetrahydrofuran and an S-5-(N-protected aminomethyl)-2-lower alkoxytetrahydrofuran, said lower alkoxy having up to four carbon atoms and said N-protecting group being stable to acid and removable with base, in an inert organic solvent and in the presence of acid;

and when said lactol derivative is S-5-(azidomethyl)-2-lower alkoxytetrahydrofuran followed by reaction of the thereby formed N-protected-O-protected-4-O-(2,3,5-trideoxy-5-azidomethylpentofuranosyl)-6-O-aminoglycosyl-1,3-diaminocyclitol with a reducing agent;

thence removal of the N-protecting and O-protecting groups from the resulting N-protected-O-protected-4-O-(2,3,5-trideoxy-5-aminomethyl (or N-protected aminomethyl)-α-D-pentofuranosyl)-6-O-aminoglycosyl-1,3-diaminocyclitol.

7. The process of claim 6 wherein said lactol derivative is an S-5-(azidomethyl)-2-lower alkoxytetrahydrofuran.

8. The process of claim 6 wherein said lactol derivative is S-5-(azidomethyl)-2-ethoxytetrahydrofuran, said inert solvent is benzene, and said acid is p-toluenesulfonic acid.

9. The process of claims 6 or 8 wherein said N-protected-O-protected-6-O-aminoglycosyl-2-deoxystreptamine is N-protected-O-protected-6-O-garosaminyl-2-deoxystreptamine whereby is produced 4-O-(2,3,5-trideoxy-5-amino-α-D-pentofuranosyl)-6-O-garosaminyl-2-deoxystreptamine.

10. A 1,3,3″-tri-N-protected-5,2″, 4‴-tri-O-protected-[4-O-(2,3,5-trideoxy-5-azido-α-D-pentofuranosyl)-6-O-aminoglycosyl]-1,3-diaminocyclitol] wherein said 6-O-aminoglycosyl is a member selected from the group consisting of garosaminyl, 3-desmethylgarosaminyl, 4-desmethylgarosaminyl, 4-desmethyl-4-epigarosaminyl, 3,4-bisdesmethylgarosaminyl, and 3,4-bisdesmethyl-4-epigarosaminyl, and wherein said 1,3-diaminocyclitol is 2-deoxystreptamine or a 5-epi-, 5-deoxy-, 5-fluoro-5-deoxy-, 5-epi-fluoro-5-deoxy-, 5-epi-azido-5-deoxy- or a 5-epi-amino-5-deoxy- derivative thereof, said N- and O-protecting groups being stable to acid and removable by treatment with base.

11. A compound of claim 10 wherein said N-protecting groups are benzyloxycarbonyl and said O-protecting groups are acetyl.

12. A compound of claim 11 which is 1,3,3′-tri-N-benzyloxycarbonyl-5,2″, 4‴-tri-O-acetyl-[4-O-(2,3,5-trideoxy-5-azido-α-D-pentofuranosyl)-6-O-aminoglycosyl-2-deoxystreptamine].

13. The method of eliciting an antibacterial response in a warm-blooded animal having a susceptible bacterial infection which comprises administering to said animal a non-toxic, antibacterially effective amount of a 4-O-(2,3,5-trideoxy-5-amino-α-D-pentofuranosyl)-6-O-aminoglycosyl-1,3-diaminocyclitol of claim 1.

14. A pharmaceutical composition comprising a non-toxic, antibacterially effective amount of a 4-O-(2,3,5-trideoxy-5-amino-α-D-pentofuranosyl)-6-O-aminoglycosyl-1,3-diaminocyclitol of claim 1 together with a non-toxic, pharmaceutically acceptable carrier.

* * * * *